US012807755B2

(12) United States Patent
Robinson et al.

(10) Patent No.: US 12,807,755 B2
(45) Date of Patent: Nov. 24, 2026

(54) POLYALKYLENE GLYCOL TERMINATED POLY-CARBODIIMIDES, AND PROCESS FOR FORMING SAME

(71) Applicant: Evoco Limited, Toronto (CA)

(72) Inventors: Jason James Robinson, Toronto (CA); Alexandros Vasileiou, Toronto (CA); Janhu Ho, Woodbridge (CA); Zhifang Zhang, Toronto (CA); Guerino Sacripante, Oakville (CA)

(73) Assignee: Evoco Limited, Toronto (CA)

( * ) Notice: Subject to any disclaimer, the term of this patent is extended or adjusted under 35 U.S.C. 154(b) by 0 days.

(21) Appl. No.: 18/823,137

(22) Filed: Sep. 3, 2024

(65) Prior Publication Data

US 2026/0062511 A1 Mar. 5, 2026

(51) Int. Cl.

| | |
|---|---|
| ***C08G 18/64*** | (2006.01) |
| ***C07C 267/00*** | (2006.01) |
| ***C08G 81/00*** | (2006.01) |
| ***C09J 5/00*** | (2006.01) |
| ***C09J 175/04*** | (2006.01) |
| ***D06N 3/00*** | (2006.01) |
| ***D06N 3/14*** | (2006.01) |
| ***D06N 3/18*** | (2006.01) |

(52) U.S. Cl.

CPC ........ *C08G 18/6415* (2013.01); *C07C 267/00* (2013.01); *C08G 81/00* (2013.01); *C09J 5/00* (2013.01); *C09J 175/04* (2013.01); *D06N 3/0006* (2013.01); *D06N 3/0047* (2013.01); *D06N 3/0095* (2013.01); *D06N 3/14* (2013.01); *D06N 3/183* (2013.01); *D06N 2209/10* (2013.01)

(58) Field of Classification Search

None

See application file for complete search history.

(56) References Cited

U.S. PATENT DOCUMENTS

| | | | | |
|---|---|---|---|---|
| 5,856,014 | A * | 1/1999 | Imashiro | C09D 167/00 524/195 |
| 5,859,166 | A | 1/1999 | Sasaki | |
| 5,958,516 | A | 9/1999 | Imashiro | |
| 6,124,398 | A | 9/2000 | Imashiro | |
| 6,127,029 | A | 10/2000 | Imashiro | |
| 6,127,477 | A | 10/2000 | Imashiro | |
| 7,439,316 | B2 | 10/2008 | Hesselmans | |
| 11,214,539 | B1 * | 1/2022 | Robinson | C08G 18/7678 |
| 11,358,929 | B1 * | 6/2022 | Robinson | C08G 18/7614 |
| 2009/0246393 | A1 | 10/2009 | Ambrose | |
| 2011/0021679 | A1 | 1/2011 | Takahashi | |
| 2022/0356150 | A1 | 11/2022 | Robinson | |
| 2023/0219322 | A1 | 7/2023 | Yamane | |
| 2023/0323005 | A1 | 10/2023 | Tsukamoto | |
| 2023/0348716 | A1 | 11/2023 | Tsukamoto | |

FOREIGN PATENT DOCUMENTS

| | | |
|---|---|---|
| EP | 2360196 | 8/2011 |
| EP | 3757146 | 12/2020 |
| EP | 3875538 | 9/2021 |

OTHER PUBLICATIONS

Gnanasekar, P., et al. "Substainable Shape-Memory Polyurethane from Abietic Acid: Superior Mechanical Properties and Shape Recovery with Tunable Transition Temperatures", ChemSusChem, 2020, vol. 13 pp. 5759-5761.

International Search Report and Written Opinion issued in respect of PCT/CA2024/051180, mailed May 14, 2025.

International Search Report mailed Dec. 1, 2025 in related International Patent Application No. PCT/CA2025/051154 (3 pages).

Written Opinion of the International Searching Authority mailed Dec. 1, 2025 in related International Patent Application No. PCT/CA2025/051154 (6 pages).

Tawade et al. Biobased Di-/Poly-isocyanates For Polyurethanes: An Overview. Polyurethanes Today, published Dec. 2017, pp. 41-46.

Third Party Observations filed Jun. 5, 2026 in related International Patent Application No. PCT/CA2025/051154 (7 pages).

Third Party Observations filed Jun. 8, 2026 in related International Patent Application No. PCT/CA2024/051180 (8 pages).

Office Action (Non-Final Rejection) dated Jul. 24, 2026 for U.S. Appl. No. 19/331,974 (pp. 1-23).

* cited by examiner

*Primary Examiner* — Arti Singh-Pandey

(57) ABSTRACT

A polyalkylene glycol terminated poly-carbodiimide has formula 1:

1

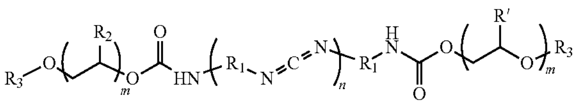

$R_1$ is an aliphatic group from about 5 to about 12 carbon atoms, a cycloaliphatic moiety of from about 6 to about 20 carbon atoms, an isosorbide moiety, a 1,3-furan moiety, an L-lysine alkyl ester moiety, a rosin moiety, a cycloaliphatic unsaturated moiety, or a cardanol moiety; $R_2$ is hydrogen or a methyl group; $R_3$ is a methyl, ethyl, or propyl moeity; and n and m are integers and are each independently between 1 and about 30.

20 Claims, 4 Drawing Sheets

5a

5b

6a

6b

7

8

9a

9b

10

11a

11b

POLYALKYLENE GLYCOL TERMINATED POLY-CARBODIIMIDES, AND PROCESS FOR FORMING SAME

FIELD

The present invention relates generally to carbodiimide stabilizers and/or crosslinkers, and in particular, to polyalkylene glycol terminated poly-carbodiimides and a process for forming same.

BACKGROUND

Carbodiimides are known in the art as providing conjugation to carboxylic acids (—COOH), such as those occurring in proteins and other in polymers such as polyester, to provide crosslinking of said polymers or conjugation with other polymers such as polyamides, polyurethane or polyamines with amine functional end groups, resulting in amide linkages. Carbodiimides also offer the most popular and versatile means to provide a stabilizer agent or a self-healing agent for polymers that degrade through ageing or hydrolysis, in which carboxylic acid groups are generated, and can be subsequently re-polymerized by the carbodiimide.

Aqueous resins as well as aqueous resin dispersions, such as polyurethane aqueous dispersions, are used in many fields such as paints, inks, fiber treatment agents, adhesives, sealants, coatings, and plant-based leather alternatives, but often exhibit inferior water resistance due to ageing and/or hydrolysis. To improve the water resistance of the aqueous resin or aqueous resin dispersion, aqueous based carbodiimides or poly-carbodiimides are conventionally employed as a crosslinker to react with functional groups such as carboxylic acid groups present in the aqueous resin or resin dispersion. In some instances, it is necessary to carry out the crosslinking reaction by heating. In many instances, an excess carbodiimide is utilized, so that any residual unreacted (namely, un-crosslinked) carbodiimide acts as a residual stabilizer dispersed within the polymer. During subsequent ageing of the polymer, degradation due to hydrolytic instability typically results in hydrolysis of the polymer and generates carboxylic acid groups, which react with the residual carbodiimide stabilizer to crosslink the polymer.

Aqueous polyurethane dispersions (PUD), sometimes referred to as “waterborne” polyurethane dispersions, are binary colloidal systems in which submicron-sized polyurethane particles are dispersed in a continuous aqueous medium. Aqueous polyurethane dispersions typically contain no organic solvent, and thereby satisfy increased demand for solventless systems for green technology applications. Aqueous polyurethane dispersions are typically produced by a dissipation or phase inversion process, whereby water is added to a polyurethane polymer or prepolymer comprising hydrophilic (ionic) groups in the polyurethane backbone. These ionic moieties are referred to as internal emulsifiers or polyurethane ionomers, and can be for example quaternary ammonium, carboxylate, or sulfonate groups. In some instances, low boiling point-point organic solvents are utilized in the polymer/prepolymer mixture but are then removed by distillation after the aqueous dispersion is formed. Chain extenders and crosslinkers may be added, before or after the aqueous dispersion is formed, to achieve varying degrees of polymerization of the polyurethane.

For example, U.S. Pat. No. 5,859,166 generally describes hydrophilic carbodiimide synthesized from an isocyanate-terminated tetramethyl-xylylene-carbodiimide and an organic compound having a hydrophilic segment and at least one functional group reactive with an isocyanate.

U.S. Pat. No. 10,647,850 generally describes a carbodiimide-based aqueous resin crosslinking agent comprising a poly-carbodiimide (A) having substituents derived from hydrophilic organic compounds at both terminals thereof, at least one of the substituents being a substituent derived from a hydrophilic organic compound having a molecular weight of 340 or more, and a poly-carbodiimide (B) having substituents derived from organic compounds having a molecular weight of 300 or less at both terminals thereof, wherein the mass ratio [(B)/(A)] of the poly-carbodiimide (B) to the poly-carbodiimide (A) is from 20/80 to 95/5.

U.S. Pat. No. 10,738,216 generally describes a coated package comprising a coating applied to the surface of the package, the coating being derived from a composition comprising a carboxyl-containing polymer, and a poly-carbodiimide.

U.S. Pat. No. 10,011,677 generally describes a poly-carbodiimide composition comprising a reaction product of poly-isocyanate having a primary isocyanate group and alcohols, wherein the poly-carbodiimide composition includes a carbodiimide group and a uretonimine group.

U.S. Pat. No. 7,439,316 generally describes a process for preparation of stable aqueous poly-carbodiimide dispersions, to be used as crosslinking agent, which are free of organic solvents, the process comprising the steps of: reacting a poly-isocyanate in the presence of a carbodiimide catalyst to form a stable poly-carbodiimide; terminating and/or chain extending the poly-carbodiimide chain by the addition of a compound containing a hydrophilic group and one or more amine and/or hydroxyl functions during or after the poly-carbodiimide formation; and dispersing the resulting compound in water, wherein the pH is adjusted to a value between 9 and 14 by the addition of a base and/or a buffer to the water used for the dispersion and/or to the obtained aqueous dispersion; and wherein said terminating or chain extending with the compound containing a hydrophilic group and one or more amine functions occurs during or after the dispersion of the poly-carbodiimide in water.

Improvements are generally desired. It is therefore an object at least to provide novel polyalkylene glycol terminated poly-carbodiimides, and a process for forming same.

SUMMARY

This disclosure is directed to an aqueous soluble biobased carbodiimide or poly-carbodiimide for use in industry as a polymer crosslinker and/or stabilizer against hydrolysis and ageing, and a production method therefor.

Conventional aqueous soluble carbodiimide or poly-carbodiimide are mainly derived from diisocyanates, organic alcohols, and amines with a catalyst. One or more of these materials are conventionally obtained from fossil fuels and therefore their production contributes heavily towards greenhouse gases that accelerate climate change and negatively impact the environment. There is a need for aqueous carbodiimide or poly-carbodiimide that have components based on renewable resource materials derived primarily from biomass, such that there is less dependency on fossil fuels.

There is also a need to provide an aqueous soluble or dispersible biobased carbodiimide or poly-carbodiimide as crosslinker and/or stabilizer, especially for use with aqueous resin dispersions such as aqueous polyurethane dispersions for applications for coatings, adhesives, ink binder, glass fibers, paper sizing, biomaterials, membranes, films for packaging, waterproof textiles, and plant-based leather alternatives (PBLA).

There is also a need for aqueous polyurethane dispersions that are derived primarily from biomass-based materials, such as biobased polyols and preferably biobased diisocyanates, and wherein no organic solvents are present in the aqueous polyurethane dispersion, and wherein the dispersion is crosslinked and/or stabilized with a water soluble biobased carbodiimide or poly-carbodiimide.

The biobased carbodiimide of the present invention is an aqueous soluble biobased carbodiimide or poly-carbodiimide, and is derived from decarboxylation of a biobased diisocyanate with a carbodiimidization catalyst to form a poly-carbodiimide, followed by condensation with a hydrophilic biobased monofunctional polyalkylene glycol having at least one reactive hydroxyl group, and with an alkoxyl group at one end to yield a poly-carbodiimide terminated with a polyalkylene glycol. The poly-carbodiimide is aqueous soluble, and is particularly useful for crosslinking and stabilization of aqueous polyurethane dispersions utilized in applications for coatings, adhesives, ink binder, glass fibers, paper sizing, biomaterials, membranes, films for packaging, waterproof textiles, and plant-based leather alternatives (PBLA).

Plant-based leather alternatives are materials intended to serve as substitutes for natural (namely, animal-based) leather for use in upholstery, clothing, footwear, and other uses in which a leather-like finish is desired. Plant-based leather is sometimes referred to as leatherette, imitation leather, faux leather, vegan leather, or PU leather.

Accordingly, in one aspect, there is provided a polyalkylene glycol terminated poly-carbodiimide of formula 1: where: $R_1$ is an aliphatic group from about 5 to about 12 carbon atoms, a cycloaliphatic moiety of from about 6 to about 20 carbon atoms, an isosorbide moiety, a 1,3-furan moiety, an L-lysine alkyl ester moiety, a rosin moiety, a cycloaliphatic unsaturated moiety, or a cardanol moiety; $R_2$ is hydrogen or a methyl group; $R_3$ is a methyl, ethyl, or propyl moeity; and n and m are integers and are each independently between 1 and about 30.

$R_1$ may be an isosorbide moiety of formula 6a or 6b. $R_1$ may be a 1,3-furan moiety of formula 7. $R_1$ may be an L-lysine moiety of formula 8, where $R_4$ is $CH_3$ or $CH_2CH_3$. $R_1$ may be a rosin moiety of formula 9a or 9b, where $R_4$ is $CH_2$ or $CH_3$; or where $R_4$ is $CH_2$, $CH_2CH_2$ or $CH_2CH_2CH_2$. $R_1$ may be a cycloaliphatic unsaturated moiety of formula 10. $R_1$ may be a cardanol moiety of formula 11a or 11b, where $R_4$ is alkyl, and R is pentadecyl; or where $R_4$ is $CH_2$, $CH_2CH_2$ or $CH_2CH_2CH_2$, and R is pentadecyl.

The polyalkylene glycol terminated poly-carbodiimide may be aqueous soluble or dispersible in water.

In one embodiment, there is provided a process for the preparation of the polyalkylene glycol terminated poly-carbodiimide, comprising the steps of: (i) decarboxylation of a diisocyanate with an alkylated phospholene oxide catalyst to yield a poly-carbodiimide; and (ii) condensation of the poly-carbodiimide with a hydrophilic monofunctional polyalkylene glycol to yield the polyalkylene glycol terminated poly-carbodiimide of formula 1.

The diisocyanate may be the biobased diisocyanate of formula 2. The alkylated phospholene oxide catalyst may be at least one of: 1-phenyl-2-phospholene-1-oxide, 3-methyl-2-phospholene-1-oxide, 1-ethyl-2-phospholene-1-oxide, 1-ethyl-3-methyl-2-phospholene-1-oxide, 3-methyl-1-phenyl-2-phospholene-1-oxide, 1-methyl-phospholene-1-oxide and 3-phospholene isomers thereof, and mixtures thereof. The poly-carbodiimide may be the poly-carbodiimide of formula 3. The hydrophilic monofunctional polyalkylene glycol may be the hydrophilic biobased monofunctional polyalkylene glycol of formula 4.

In another embodiment, there is provided a use of the polyalkylene glycol terminated poly-carbodiimide as a crosslinking agent in an aqueous polyester resin dispersion or in an aqueous polyurethane dispersion.

In another embodiment, there is provided a use of the polyalkylene glycol terminated poly-carbodiimide as a stabilizing agent in an aqueous polyester resin dispersion or in an aqueous polyurethane dispersion.

In still another embodiment, there is provided an artificial leather comprising: a fabric layer; an adhesive layer; a foam layer; and a topcoat layer, wherein the adhesive layer, the foam layer and the topcoat layer are each formed from an aqueous polyurethane dispersion, and wherein at least one of the adhesive layer, the foam layer and the topcoat layer is further formed from the polyalkylene glycol terminated poly-carbodiimide.

Each of the adhesive layer, the foam layer and the topcoat layer may be further formed from the polyalkylene glycol terminated poly-carbodiimide. Each of the adhesive layer, the foam layer and the topcoat layer may be formed from a different the polyalkylene glycol terminated poly-carbodiimide.

In another embodiment, there is provided a method of forming the artificial leather, comprising: forming the topcoat layer by depositing a topcoat mixture comprising a first aqueous polyurethane dispersion, and optionally the polyalkylene glycol terminated poly-carbodiimide, onto a substrate and drying the topcoat mixture; forming the foam layer by depositing a foam layer mixture comprising a second aqueous polyurethane dispersion, and optionally the polyalkylene glycol terminated poly-carbodiimide, onto the topcoat layer and drying the foam layer mixture; forming the adhesive layer by: depositing an adhesive layer mixture comprising a third aqueous polyurethane dispersion, and optionally the polyalkylene glycol terminated poly-carbodiimide, onto the foam layer, applying the fabric layer to the deposited adhesive layer mixture, and drying the adhesive layer mixture.

At least two of the first aqueous polyurethane dispersion, the second aqueous polyurethane dispersion and the third aqueous polyurethane dispersion may be the same.

The first aqueous polyurethane dispersion, the second aqueous polyurethane dispersion and the third aqueous polyurethane dispersion may be the same.

Forming the adhesive layer further may comprise applying pressure to the fabric layer to improve adhesion.

The method may further comprise mechanically frothing the foam layer mixture prior to said depositing the foam layer mixture.

The method may further comprise separating the topcoat layer, the foam layer, the adhesive layer and the fabric layer as a unitary material from the substrate.

BRIEF DESCRIPTION OF THE DRAWINGS

Embodiments will now be described more fully with reference to the accompanying drawings in which.

DETAILED DESCRIPTION OF THE INVENTION

The present invention is directed to aqueous soluble carbodiimide or poly-carbodiimide, wherein the poly-carbodiimide is terminated with a hydrophilic polyalkylene glycol moiety. The poly-carbodiimide is derived from decarboxylation of a biobased diisocyanate with a carbodiimidization catalyst such as an alkylated phospholene oxide to form a poly-carbodiimide, followed by condensation with a hydrophilic biobased monofunctional polyalkylene glycol having at least one reactive hydroxyl group, and having an alkoxyl group at one end, to yield a poly-carbodiimide terminated with a polyalkylene glycol of formula 1, shown in FIG. 1. The polyalkylene glycol terminated poly-carbodiimide of formula 1 is aqueous soluble, and can be dispersed or dissolved in water utilizing a base and/or a buffer such that the pH is adjusted to a value of between 9 and 14. The poly-carbodiimide may be used as a crosslinker and/or stabilizer, for example with an aqueous polyurethane dispersion, for plant-based leather alternative (PBLA) coatings, adhesives, sheet materials, and the like.

As will be understood, stabilizers are additives that are added to polymeric materials, such as plastics and rubbers, to inhibit or retard their degradation. In contrast, crosslinkers are additives that are added to polymeric materials to promote linking between polymer chains to adjust the mechanical properties of the polymer by a desired amount.

Figure 1:
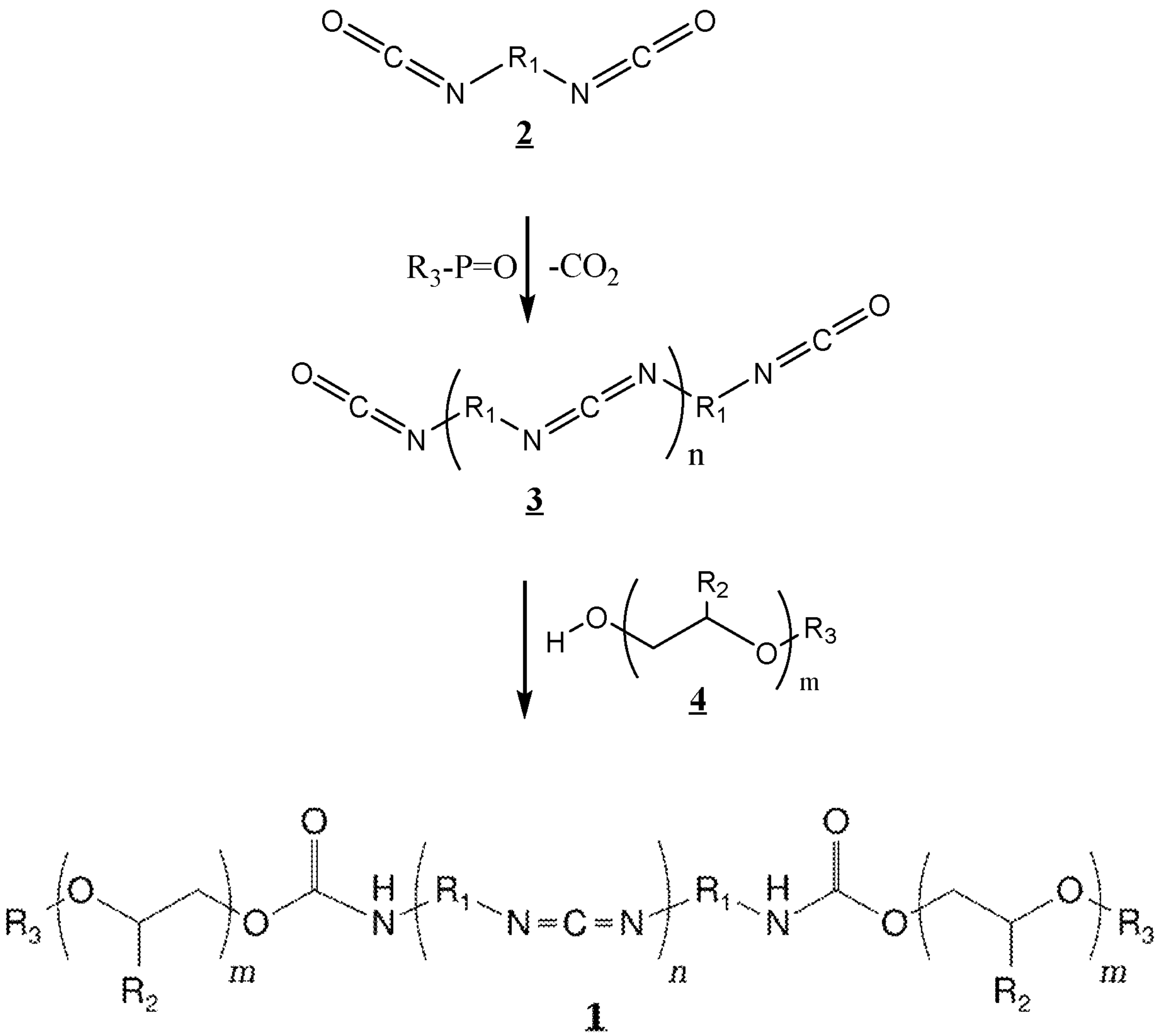
FIG. 1 is a structural view of a poly-carbodiimide of formula 1.
Figure 2A:
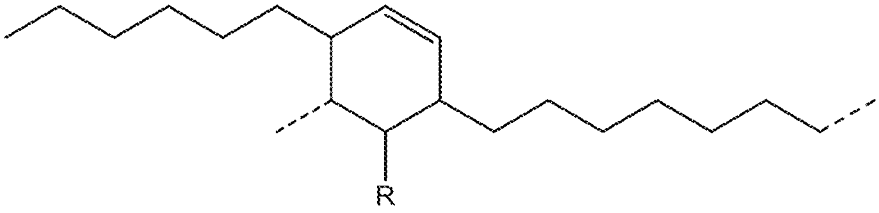
FIGS. 2A and 2B are structural views of possible organic moieties $R_1$ of formula 1.
Figure 2A:
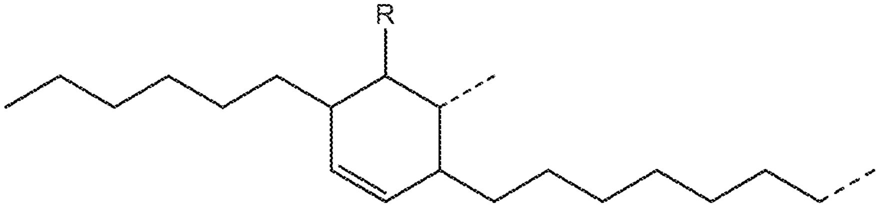
Figure 2A:
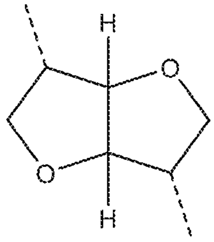
Figure 2A:
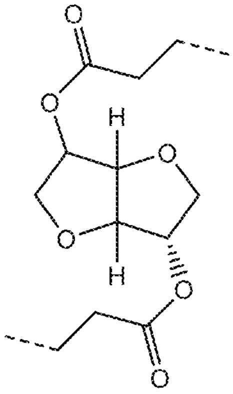
Figure 2A:
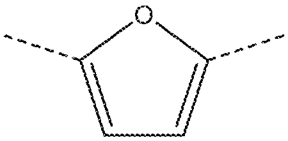
Figure 2A:
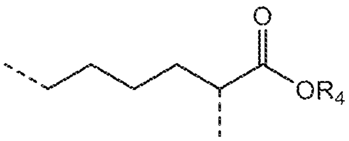
Figure 2B:
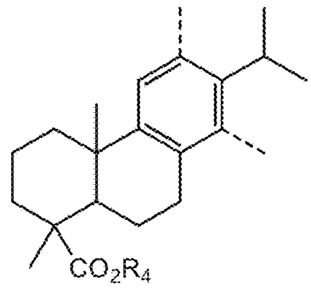
Figure 2B:
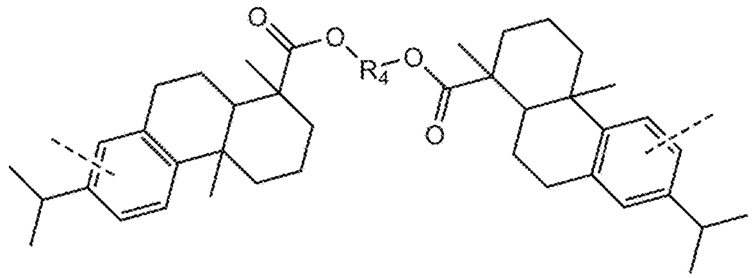
Figure 2B:
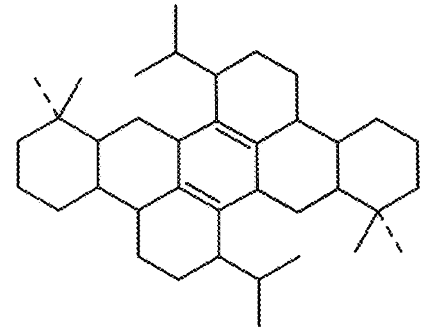
Figure 2B:
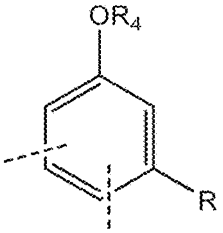
Figure 2B:
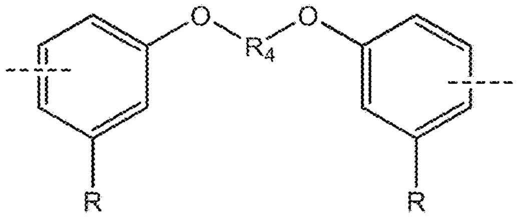

FIG. 1 shows the polyalkylene glycol terminated poly-carbodiimide of formula 1 of the present invention, and one approach used for its synthesis. The poly-carbodiimide of formula 1 is preferably obtained by decarboxylation of the biobased diisocyanate of formula 2, utilizing an alkylated phospholene oxide catalyst to yield the poly-carbodiimide of formula 3. The poly-carbodiimide of formula 3 may then be condensed with a hydrophilic biobased monofunctional polyalkylene glycol of formula 4 to yield the polyalkylene glycol terminated poly-carbodiimide of formula 1, wherein $R_1$ may be an aliphatic moiety from about 5 to about 12 carbon atoms, a cycloaliphatic moiety of from about 6 to about 20 carbon atoms (such as, for example, that of formula 5a or 5b), an isosorbide moiety (such as, for example, that of formula 6a or 6b), a 1,3-furan moiety (such as, for example, that of formula 7), an L-lysine alkyl ester moiety (such as, for example, that of formula 8), a rosin moiety (such as, for example, that of formula 9a or 9b), a cycloaliphatic unsaturated moiety (such as, for example, that of formula 10), or a cardanol moiety (such as, for example, that of formula 11a or 11b); $R_2$ is hydrogen or a methyl moiety; $R_3$ is a methyl, ethyl or propyl moiety; and n and m are integers representing the number of segments and are each independently between 1 and about 100, or preferably between 1 and about 30. The exemplary formulas 5a through 11b are shown in FIGS. 2A and 2B.

In some embodiments, the polyalkylene glycol terminated poly-carbodiimide of formula 1 is prepared by reacting poly(alkylene oxide) alkyl ether (such as the hydrophilic biobased monofunctional polyalkylene glycol of formula 4) with diisocyanate (such as the biobased diisocyanate of formula 2) and a catalyst (such as the alkylated phospholene oxide catalyst shown in FIG. 1) at a temperature of from about 90° C. to about 200° C., preferably at a temperature of from about 100° C. to about 200° C., and more preferably at a temperature of from about 120° C. to about 200° C., for a duration of from about 1 to about 10 hours.

Examples of the biobased diisocyanate that can be used for preparation of the poly-carbodiimide of formula 1 are those that can be obtained through a fermentation process, or chemically derived from natural (biobased) sources, and can be selected from 1,5-pentamethylene diisocyanate available as STABIO™ PDI from Mitsui Chemicals, and which is derived from biobased lysine; L-lysine methyl ester diisocyanate; L-lysine ethyl ester diisocyanate; the rosin based diisocyanates disclosed in U.S. Pat. No. 11,214,539; rosin based diisocyanates such as those described by Bingham and Marvel in "Preparation and Polymerization of a Diisocyanate from the Diels-Alder Adduct of Levopimaric Acid", Journal of Polymer Science: Part A-1, 10, p. 921 (1972), in which the Diels-Alder adduct of levopimaric acid and acrylic acid is converted to ethyl ester diisocyanate; the cardanol based diisocyanates disclosed in U.S. Pat. No. 11,358,929; bis(4-isocyanato-2-methoxyphenoxy) propane and bis(4-isocyanato-2,6-dimethoxyphenoxy) propane as disclosed in U.S. Pat. No. 9,950,996; biobased furan diisocyanate as described by Cawse et al., "Polymers from renewable sources", Die Makromolekulare Chemie, 185 (4) p. 697 (1984); aliphatic diisocyanate available as Tolonate™ X FLO 100 from Vencorex Chemicals and derived from palm oil; biobased 1,7-heptamethylene diisocyanate derived from azelaic acid; 1,8-octamethylene diisocyanate derived from biobased sebacic acid; 1,10-decamethylene diisocyanate derived from biobased dodecanedioic acid; cycloaliphatic nonadecenyl- and nonadecyl-diisocyanates as disclosed in German Patent Document No. 1992296; isosorbide based diisocyanates as described by Kessler et al., ChemSusChem 2013, 6, 1182-1185, and Aspects of Polyurethanes, "Bio-Based Polyurethanes from Carbohydrate Monomers" by Galbis et al, edited by Faris Yilmaz DOI: 10.5772/intechopen.69606; fatty acid diisocyanates derived from oleic acid as described by Narine et al., Biomacromolecules 2009, 10, 884-89; and cyclic unsaturated diisocyanate obtained from biobased abietic acid as described by Yan et al., ChemSusChem 2020, 13, 5749-5761. The biobased diisocyanate is selected in an amount of, for example, from about 35 to about 60 wt. %, and preferably from about 45 to about 50 wt. % of the polyalkylene glycol terminated poly-carbodiimide. Other biobased diisocyanates may be known and are totally incorporated herein.

Examples of the carbodiimidization catalyst include, for example, 1-phenyl-2-phospholene-1-oxide, 3-methyl-2-phospholene-1-oxide, 1-ethyl-2-phospholene-1-oxide, 1-ethyl-3-methyl-2-phospholene-1-oxide, 3-methyl-1-phenyl-2-phospholene-1-oxide, 1-methyl-phospholene-1-oxide and 3-phospholene isomers thereof. The catalysts may be in amounts of, for example, from about 0.01 to about 5 wt. %, preferably from about 0.1 to about 0.8 wt. %, and more preferably from about 0.2 to about 0.6 wt. %, based on the starting weight of the biobased diisocyanate.

Examples of the hydrophilic biobased monofunctional polyalkylene glycol, having at least one reactive hydroxyl group, and having an alkoxyl group at one end, include, for example, polyethylene glycol monomethyl ether of various molecular weights of from about 350 to about 1000 and obtained from various sources such as mPEG 350, mPEG 1000 and mPEG 5000, polypropylene glycol mono-methyl ether, copoly-(ethylene glycol)-copoly-(propylene glycol) mono-methyl ether, polypropylene glycol mono-ethyl ether, copoly-(ethylene glycol)-copoly-(propylene glycol) mono-ethyl ether, mixtures thereof, and the like. The biobased monofunctional polyalkylene glycol may display varying molecular weights such as from about 120 g/mol to about 5,000 g/mol, and is selected in an amount of, for example, from about 10 to about 60 wt. %, and preferably from about 45 to about 50 wt. %, of the polyalkylene glycol terminated poly-carbodiimide.

Figure 3:
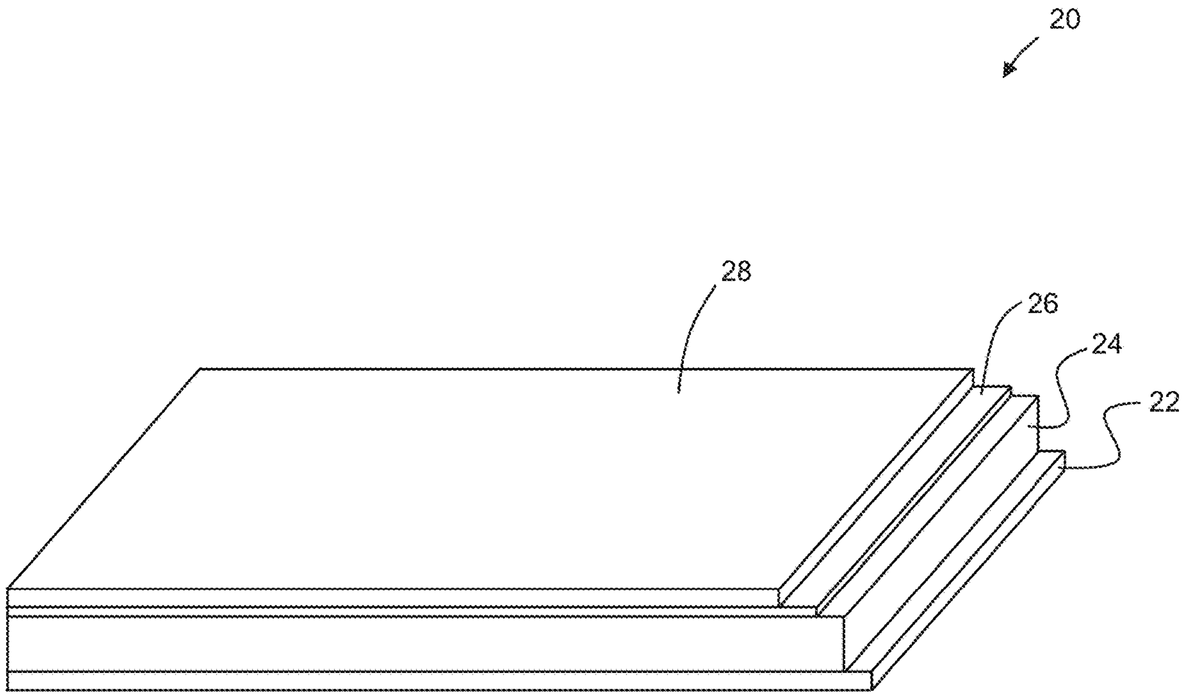
FIG. 3 is a schematic view of an exemplary plant-based leather alternative (PBLA) swatch prepared using a polyurethane dispersion (PUD) and the poly-carbodiimide of formula 1.

Plant-based leather alternative (PBLA) can be prepared using a polyurethane dispersion (PUD) and the polyalkylene glycol terminated poly-carbodiimide of formula 1. FIG. 3 shows a schematic diagram of a swatch of PBLA prepared from such materials, which is generally indicated by reference numeral 20. PBLA swatch 20 consists of the standard three polyurethane (PU) layers typical of synthetic leather, namely a topcoat layer 22, a foam layer 24, and a "binder" or adhesive layer 26. A non-PUD, woven textile layer 28 is typically affixed to the adhesive layer 26 to provide mechanical integrity and support to the PBLA.

The procedure for producing PBLA in the present invention, such as PBLA swatch 20, involves forming a mixture for each layer 22, 24 or 26 comprising: i) one or more PUDs, ii) optionally the poly-carbodiimide of formula 1, and iii) other additives such as fillers, foaming agent, defoamer, dyes, wetting agents, and the like, suitable or appropriate for forming the standard three polyurethane (PU) layers 22, 24 and 26. The mixtures are then sequentially cast and formed in a layer-by-layer manner to form the PBLA. The PUD (or PUDs) used for each of the layers 22, 24 and 26 can be the same or different. Preferably, the PUDs are bioderived, such as those disclosed in U.S. Pat. No. 11,530,332, and are formulated such that they are suitable for use in the topcoat layer 22, the foam layer 24 and the adhesive layer 26.

In the casting process, a topcoat mixture is first coated onto a suitable surface or substrate, such as casting paper, using a suitable coating device or apparatus. The topcoat mixture is then dried at a suitable temperature, such as between 8° and 120° C., for a suitable time, such as between 1 and 20 minutes, to yield the topcoat layer 22. A foam layer mixture is then provided and mechanically frothed and coated on top of the topcoat layer 22, or optionally onto an intermediate layer such as a binder or adhesive layer (not shown), using a suitable coating device or apparatus. The foam layer is then dried at a suitable temperature, such as between 8° and 120° C., for a suitable time, such as between 1 and 20 minutes, to yield the foam layer 24. Next, a polyurethane dispersion (PUD) binder (adhesive) layer mixture is applied onto the foam layer 24 using a suitable coating device or apparatus, and a woven textile layer 28, such as a 100% cotton fabric or other fabric, is placed on top of the coating of the binder (adhesive) layer mixture. Pressure is applied by a suitable tool, such as a press, a roller, a rolling pin, and the like, to ensure proper adhesion. The layer stack is then dried at a suitable temperature, such as between 8° and 120° C., for a suitable time, such as between 1 and 20 minutes, to yield the PBLA swatch 20 disposed on the substrate and having the standard three polyurethane (PU) layers, namely the topcoat layer 22, the foam layer 24, and the adhesive layer 26. The PBLA swatch 20 may then be separated from the substrate by a suitable technique, such as peeling, substrate dissolution, and the like.

Specific embodiments of the present disclosure as illustrated in the following Examples are for illustrative purposes and are not limited to the materials, conditions, or process parameters set forth in these embodiments.

Example 1 (Comparative)

Preparation of Poly-(Triethylene Glycol) Mono Methyl Ether Terminated Poly-Carbodiimide of Formula 1, where R is $(CH_2)_6$, $R_2$ is H, $R_3$ is $CH_3$, and m is 3.

A reaction apparatus comprising a 250 mL three-neck round-bottom flask equipped with a mixing blade, a condenser, and a silicone oil bath was prepared. Approximately 16.5 g of triethylene glycol monomethyl ether along with 0.61 g of catalyst (3-methyl-1-phenyl-2-phospholene 1-oxide) was weighed and added into the 250 mL round bottom flask. Approximately 35 mL of hexamethylene diisocyanate (HDI) was pipetted into the mixture. The 0.61 g catalyst corresponded to about 2 wt. % of the HDI. The contents of the flask were mixed for 5 minutes at room temperature. The reaction was heated to 120° C. for 1 hour. At 1 hour, the originally clear, colorless was a yellow color, and the NCO content was measured as 18% (note: pure HDI has an NCO content of 49.9%). Heating at 120° C. was continued. At 4 hours, the liquid was a dark amber yellow color, and the NCO content was measured as 13.5%. At 6 hours, the reaction temperature was increased to 185° C. At 7 hours, the temperature was reduced to 120° C. and left overnight. The reaction was continued until the NCO peak at 2290 $cm^{-1}$ in the FTIR spectrum disappeared. The theoretical degree of polymerization of the resulting poly-carbodiimide was 2.

The mixture was cooled to 80° C., and deionized water was added under mixing to adjust the solids content to 40 wt. %. The pH was adjusted to 11 using a 10 wt. % aqueous NaOH solution. The NCN peak in the FTIR spectrum of the final product was identified at around 2100 $cm^{-1}$.

As will be understood, the commercially available HDI is not biobased, and therefore Example 1 can be regarded as a comparative example to Examples 2 to 4 in which biobased diisocyanates are used.

Example 2

Preparation of Poly-(Triethylene Glycol) Mono Methyl Ether Terminated Poly-Carbodiimide of Formula 1, where R is $(CH_2)_5$, $R_2$ is H, $R_3$ is $CH_3$, and m is 3.

A reaction apparatus comprising a 250 mL three-neck round-bottom flask equipped with a mixing blade, a condenser, and a silicone oil bath was prepared. About 0.61 g of catalyst (3-methyl-1-phenyl-2-phospholene 1-oxide), 30.83 g (~0.2 mol) of plant-based pentamethylene diisocyanate (PDI, Mitsui Chemicals, 71% biobased carbon), and 16 g (~0.1 mol) of triethylene glycol monomethyl ether (TEG) were pre-measured and added into the 250 mL round bottom flask. The 0.61 g catalyst corresponded to about 2 wt. % of the PDI. The reaction mixture was heated to 100° C. The reaction was continued at 100° C. until the NCO peak in the FTIR spectrum at 2290 $cm^{-1}$ disappeared. The theoretical degree of polymerization of the carbodiimide compound was 2. The IR signal of the final product showed a strong NCN peak at around 2100 $cm^{-1}$. The mixture was cooled to 90° C., and deionized water was added under mixing to adjust the solids content to 45 wt. %. The pH was adjusted to 11 using a 10 wt. % aqueous NaOH solution. A translucent yellow solution was decanted into a 4 oz amber jar.

Example 3

Preparation of Poly-(Triethylene Glycol) Mono Methyl Ether Terminated Poly-Carbodiimide of Formula 1, where R is $(CH_2)_5$, $R_2$ is H, $R_3$ is $CH_3$, and m is 3.

A reaction apparatus comprising a 250 mL three-neck round-bottom flask equipped with a magnetic stir bar, a condenser, and a silicone oil bath was prepared. About 0.61 g of catalyst (3-methyl-1-phenyl-2-phospholene 1-oxide), 30.83 g (~0.2 mol) of plant-based pentamethylene diisocyanate (PDI, Mitsui Chemicals, 71% biobased carbon), and 16 g (~0.1 mol) of plant triethylene glycol monomethyl ether (bio-TEG, India Glycols, 100% biobased carbon) were pre-measured and added into the 250 mL round bottom flask. The 0.61 g catalyst corresponded to about 2 wt. % of the PDI. The reaction mixture was heated to 100° C. The reaction was continued at 100° C. until the NCO peak in the FTIR spectrum at 2290 cm 1 disappeared. The theoretical degree of polymerization of the carbodiimide compound was 2. The IR signal of the final product showed a strong NCN peak at around 2100 $cm^{-1}$. A 16 g portion of the resulting compound was removed and then cooled to 90° C. Deionized water was added to the removed portion under mixing to adjust the solids content to 45 wt. %. The pH was adjusted to 11 using a 10 wt. % aqueous NaOH solution.

Example 4

Preparation of Waterborne Polyurethane Dispersion (PUD).

To a 1 L three-necked round bottom flask equipped with a mechanical stirrer was added 0.5 mol of poly-(1,3-propylene-succinate) obtained from Panolam Industries, having a viscosity of about 3,000 cp, a hydroxyl value of 36 milligrams of KOH/gram and an acid value of 0.93 milligrams of KOH/gram. The poly-(1,3-propylene-succinate) was heated to 80° C. while mixing under nitrogen atmosphere. Once a temperature of 80° C. was reached, 0.12 mol of hexamethylene diisocyanate was added dropwise using a pressure equalizing dropping funnel. The mixture was stirred at 275 rpm, and 0.005 mol of Orgatix TC-400 catalyst (available from Matsumoto Fine Chemical) was added.

The temperature was maintained at 82° C. for about 2.5 hours, until the viscosity reached a value between about 18,000 and about 24,000 cp. The mixture was then cooled to 75° C., and 0.022 mol of 2,2 bis(hydroxymethyl) propionic acid was added. The reaction was allowed to continue for 2 hours, after which the reaction mixture was allowed to cool to about 55° C. The viscosity was then adjusted (lowered) by adding 40 mL of organic solvent (either MEK or acetone). Triethylamine (0.023 mol) was then added to the mixture to neutralize the hydrophilic moiety, followed by addition of 50 mL of organic solvent. After 30 minutes of stirring, the mixture was cooled to about 10° C. Separately, in a 500 mL Pyrex beaker, 0.042 mol of lysine was dissolved in 270 mL deionized water and cooled to 10° C. Once the mixture in the beaker reached 15° C., the stirrer speed was set to 1000 rpm and the cooled lysine/water solution was added to the reaction mixture over a 5-minute period and allowed to mix for 4 hours to complete the polymerization. Thereafter, the organic solvent was removed by distillation, and the resulting polyurethane dispersion (PUD) was cooled to room temperature. The PUD had 35 wt. % solids in water with an average particle size of 190 nanometers.

Example 5

Preparation of Thin Films Using the Waterborne Polyurethane Dispersion (PUD) Of Example 4 and the Poly-Carbodiimide of Example 3.

Thin films were produced by mixing 40 g of the polyurethane dispersion (PUD) with poly-carbodiimide (poly-CDI) as crosslinker and/or stabilizer (if any) in a plastic cup. The content(s) were mechanically stirred for at least 2 minutes using a P4 mixing blade under room temperature. The content(s) were then placed under vacuum to remove air bubbles. Once air bubbles were removed, the content(s) were poured into Teflon molds. The content(s) were spread uniformly within the mold and left to dry overnight at room temperature overnight to form samples. The samples were then placed in a drying oven at 100° C. for at least 3 hours. After cooling to room temperature overnight, the samples were separated from the mold as thin films. Dumbbell-shaped thin film specimens were cut using a hydraulic press and die, and mechanical properties were measured in accordance with ASTM D412.

The thin films were produced using the polyurethane dispersion (PUD) of Example 4 with either i) no poly-carbodiimide, ii) a commercially available poly-carbodiimide (Picassian XL 702, which is a conventional, non-plant-based poly-carbodiimide), or iii) the plant-based poly-carbodiimide of Example 3. The measured mechanical properties of these films are shown in Table 1.

TABLE 1

| Poly-CDI (solids, wt. %) | 100% modulus (MPa) | Maximum stress (MPa) | Elongation at break (%) |
|---|---|---|---|
| none (PUD only) | 0.60 ± 0.1 | 1.1 ± 0.2 | 1300 ± 50 |
| 4.5% Picassian XL 702 (commercial) | 1.9 ± 0.2 | 5.2 ± 1.7 | 450 ± 50 |
| 4.5% bio poly-CDI (Example 3) | 1.1 ± 0.1 | 2.5 ± 0.24 | 450 ± 10 |

As can be seen, an increase in modulus and stress was advantageously observed for films crosslinked and/or stabilized with the poly-carbodiimide, as compared to PUD only films.

Example 6

Preparation of PBLA Swatches Using the Thin Films of Example 5.

Plant-based leather alternative (PBLA) swatches were prepared using the PUD of Example 4 and the poly-carbodiimide (if any) as crosslinker and/or stabilizer of Example 3. Each PBLA swatch was produced by mixing the PUD with the poly-CDI (if any) and other additives (fillers, foaming agent, defoamer, dye, wetting agent, etc.) appropriate to form the standard three polyurethane (PU) layers of synthetic leather, namely a topcoat layer, a foam layer, and an adhesive layer. The materials were mechanically mixed using a P4 mixing blade. The topcoat mixture was coated onto a casting paper using a Mathis LTE-S Labcoater, and then dried at 100° C. for 3 minutes to form the topcoat layer. The foam layer mixture was mechanically frothed and coated onto the topcoat layer using the Labcoater, and then dried at 100° C. for 3 minutes to form the foam layer. The adhesive mixture was coated onto the foam layer, and a woven 100% cotton fabric was then placed thereon and a rolling pin was used to ensure proper adhesion. The stack of layers was put through a final drying cycle at 100° C. for 5 minutes in the Labcoater. The resulting dried stack was peeled off the casting paper to yield the PBLA swatch.

Three PBLA swatches were prepared, one without any poly-carbodiimide and the others with 4.5 wt. % and 9.0 wt. % (based on solids) of the poly-carbodiimide of Example 3. Hydrolytic stability of the swatches was tested at 70° C. and 95% RH in accordance with SATRA TM344, and the results are shown in Table 2.

TABLE 2

| Poly-CDI (solids, wt. %) | Hydrolytic Stability (days) |
|---|---|
| none (PUD only) | 3 |
| 4.5% bio poly-CDI Example 3) | 7 |
| 9.0% bio poly-CDI (Example 3) | 16 |

As can be seen, an increase in hydrolytic stability was advantageously observed for swatches containing PU layers crosslinked and/or stabilized by the poly-carbodiimide, as compared to the PUD only swatch. In the swatches containing PU layers crosslinked and/or stabilized by the poly-carbodiimide, hydrolytic stability was observed to advantageously increase with the amount of poly-carbodiimide.

The claims, as originally presented and as they may be amended, include alternatives, modifications, improvements, equivalents, and substantial equivalents of the disclosed embodiments and teachings, including those that are presently unforeseen, or unappreciated, and that, for example, may arise from applicants/patentees and others. Unless specifically recited in a claim, steps, or components of claims should not be implied, or imported from the specification, or any other claims as to any particular order, number, position, size, shape, angle, color, or material. Percent (%) by weight is a known quantity and is usually based on the total of the components present divided by the specific component present.

What is claimed is:

1. An artificial leather comprising:

a fabric layer;

an adhesive layer disposed directly on the fabric layer;

a foam layer disposed directly on the adhesive layer; and a topcoat layer disposed directly on the foam layer, wherein the adhesive layer, the foam layer and the topcoat layer are each formed from a first, second and third aqueous dispersion comprising polyurethane, respectively, and wherein at least one of the first, second and third aqueous dispersion further comprises a polyalkylene glycol terminated poly-carbodiimide of formula 1:

1

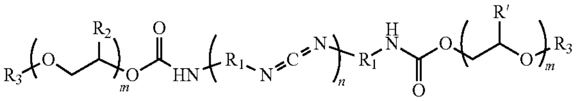

where:

$R_1$ is an aliphatic group from about 5 to about 12 carbon atoms, a cycloaliphatic moiety of from about 6 to about 20 carbon atoms, an isosorbide moiety, a 1,3-furan moiety, an L-lysine alkyl ester moiety, a rosin moiety, a cycloaliphatic unsaturated moiety, or a cardanol moiety;

$R_2$ is hydrogen or a methyl group;

$R_3$ is a methyl, ethyl, or propyl moeity; and n and m are integers and are each independently between 1 and about 30, wherein the artificial leather has a hydrolytic stability in accordance with SATRA 344 of between 3 and 16 days.

2. A method of forming the artificial leather of claim 1, comprising:

forming the topcoat layer by depositing a topcoat mixture comprising a first aqueous polyurethane dispersion, and optionally the polyalkylene glycol terminated poly-carbodiimide of formula 1, onto a substrate and drying the topcoat mixture;

forming the foam layer by depositing a foam layer mixture comprising a second aqueous polyurethane dispersion, and optionally the polyalkylene glycol terminated poly-carbodiimide of formula 1, onto the topcoat layer and drying the foam layer mixture;

forming the adhesive layer by:

depositing an adhesive layer mixture comprising a third aqueous polyurethane dispersion, and optionally the polyalkylene glycol terminated poly-carbodiimide of formula 1, onto the foam layer, applying the fabric layer to the deposited adhesive layer mixture, and drying the adhesive layer mixture.

3. The method of claim 2, wherein at least two of the first aqueous polyurethane dispersion, the second aqueous polyurethane dispersion and the third aqueous polyurethane dispersion are the same.

4. The method of claim 2, wherein the first aqueous polyurethane dispersion, the second aqueous polyurethane dispersion and the third aqueous polyurethane dispersion are the same.

5. The method of claim 4, wherein forming the adhesive layer further comprises applying pressure to the fabric layer to improve adhesion.

6. The method of claim 2, further comprising mechanically frothing the foam layer mixture prior to said depositing the foam layer mixture.

7. The method of claim 2, further comprising separating the topcoat layer, the foam layer, the adhesive layer and the fabric layer as a unitary material from the substrate.

8. The artificial leather of claim 1, wherein $R_1$ is an isosorbide moiety of formula 6*a* or 6*b*:

6a

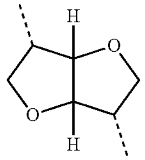

6b

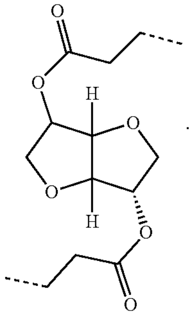

9. The artificial leather of claim 1, wherein $R_1$ is a 1,3-furan moiety of formula 7:

7

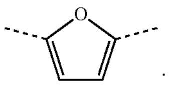

10. The artificial leather of claim 1, wherein $R_1$ is an L-lysine moiety of formula 8:

8

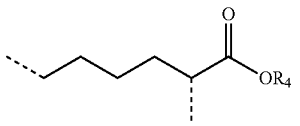

where $R_4$ is $CH_3$ or $CH_2CH_3$.

11. The artificial leather of claim 1, wherein $R_1$ is a rosin moiety of formula 9*a* or 9*b*:

9a

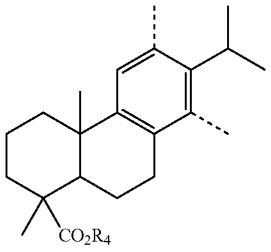

where $R_4$ is $CH_2$ or $CH_3$; or

9b

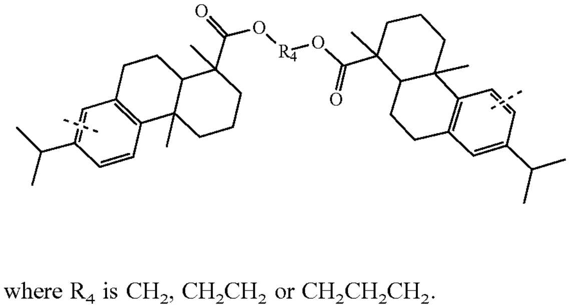

where $R_4$ is $CH_2$, $CH_2CH_2$ or $CH_2CH_2CH_2$.

12. The artificial leather of claim 1, wherein $R_1$ is a cycloaliphatic unsaturated moiety of formula 10:

10

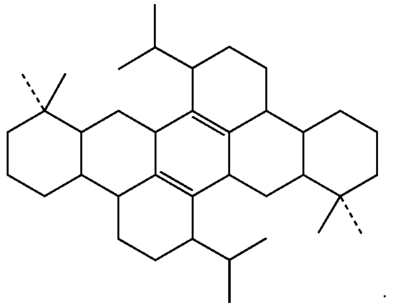

13. The artificial leather of claim 1, wherein $R_1$ is a cardanol moiety of formula 11*a* or 11*b*:

11a

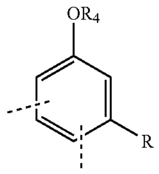

where $R_4$ is alkyl, and R is pentadecyl; or

11b

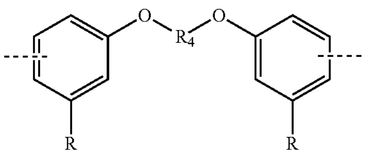

where $R_4$ is $CH_2$, $CH_2CH_2$ or $CH_2CH_2CH_2$, and R is pentadecyl.

14. The artificial leather of claim 1, wherein at least two of the first aqueous polyurethane dispersion, the second aqueous polyurethane dispersion and the third aqueous polyurethane dispersion are the same.

15. The artificial leather of claim 1, wherein the first aqueous polyurethane dispersion, the second aqueous polyurethane dispersion and the third aqueous polyurethane dispersion are the same.

16. An artificial leather comprising:

a fabric layer;

a single adhesive layer;

a foam layer; and a topcoat layer, wherein the single adhesive layer is the only adhesive layer between the fabric layer and the topcoat layer, and wherein the adhesive layer, the foam layer and the topcoat layer are each formed from a first, second and third aqueous dispersion comprising polyurethane, respectively, and wherein at least one of the first, second and third aqueous dispersion further comprises a polyalkylene glycol terminated poly-carbodiimide of formula 1:

1

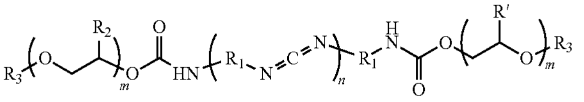

where $R_1$ is an aliphatic group from about 5 to about 12 carbon atoms, a cycloaliphatic moiety of from about 6 to about 20 carbon atoms, an isosorbide moiety, a 1,3-furan moiety, an L-lysine alkyl ester moiety, a rosin moiety, a cycloaliphatic unsaturated moiety, or a cardanol moiety;

$R_2$ is hydrogen or a methyl group;

$R_3$ is a methyl, ethyl, or propyl moeity; and n and m are integers and are each independently between 1 and about 30, wherein the artificial leather has a hydrolytic stability in accordance with SATRA 344 of between 3 and 16 days.

17. The artificial leather of claim 16, wherein at least two of the first aqueous polyurethane dispersion, the second aqueous polyurethane dispersion and the third aqueous polyurethane dispersion are the same.

18. The artificial leather of claim 16, wherein the first aqueous polyurethane dispersion, the second aqueous polyurethane dispersion and the third aqueous polyurethane dispersion are the same.

19. The artificial leather of claim 16, wherein $R_1$ is an isosorbide moiety of formula 6*a* or 6*b*:

6a

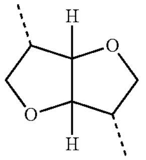

-continued

6b

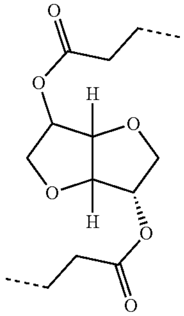

.

20. The artificial leather of claim 16, wherein $R_1$ is a cardanol moiety of formula 11*a* or 11*b*:

11a

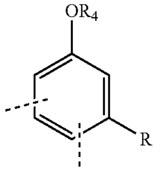

where $R_4$ is alkyl, and R is pentadecyl; or

11b

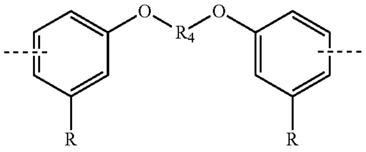

where $R_4$ is $CH_2$, $CH_2CH_2$ or $CH_2CH_2CH_2$, and R is pentadecyl.

* * * * *